United States Patent
Glaser-Seidnitzer et al.

(10) Patent No.: US 8,350,809 B2
(45) Date of Patent: Jan. 8, 2013

(54) INPUT DEVICE TO CONTROL ELEMENTS OF GRAPHICAL USER INTERFACES

(75) Inventors: Karlheinz Glaser-Seidnitzer, Fürth (DE); Johannes Kling, Zurich (CH)

(73) Assignee: Siemens Aktiengesellschaft, Munich (DE)

( * ) Notice: Subject to any disclaimer, the term of this patent is extended or adjusted under 35 U.S.C. 154(b) by 420 days.

(21) Appl. No.: 12/420,175

(22) Filed: Apr. 8, 2009

(65) Prior Publication Data

US 2009/0273564 A1 Nov. 5, 2009

(30) Foreign Application Priority Data

Apr. 8, 2008 (DE) .......................... 10 2008 017 832

(51) Int. Cl.
*G06F 3/033* (2006.01)

(52) U.S. Cl. ........ 345/161; 345/156; 345/159; 345/163; 345/164

(58) Field of Classification Search .................. None
See application file for complete search history.

(56) References Cited

U.S. PATENT DOCUMENTS

| | | | | |
|---|---|---|---|---|
| 5,558,329 A * | 9/1996 | Liu | ............................ | 273/148 B |
| 5,786,807 A * | 7/1998 | Couch et al. | .................. | 345/161 |
| 6,068,554 A * | 5/2000 | Tyler | ................................ | 463/38 |
| 6,115,028 A * | 9/2000 | Balakrishnan et al. | ........ | 345/157 |
| 6,128,006 A * | 10/2000 | Rosenberg et al. | ............ | 345/163 |
| 6,577,298 B2 * | 6/2003 | Krog | ............................ | 345/161 |
| 6,580,418 B1 * | 6/2003 | Grome et al. | .................. | 345/161 |
| 6,624,806 B2 * | 9/2003 | Hsu | ................................ | 345/161 |
| 6,954,198 B2 * | 10/2005 | Shih et al. | ...................... | 345/163 |
| 7,209,119 B2 * | 4/2007 | Oguro | ............................ | 345/161 |
| 7,463,241 B2 * | 12/2008 | Ushimaru et al. | ............. | 345/161 |
| 8,100,218 B2 * | 1/2012 | Case et al. | ..................... | 180/333 |
| 2002/0054015 A1 * | 5/2002 | Wingett et al. | ............... | 345/156 |
| 2004/0041787 A1 * | 3/2004 | Graves | .......................... | 345/157 |
| 2004/0041792 A1 * | 3/2004 | Criscione | ...................... | 345/169 |
| 2006/0250353 A1 | 11/2006 | Yasutake | | |
| 2007/0233289 A1 * | 10/2007 | Arai et al. | ....................... | 700/85 |

FOREIGN PATENT DOCUMENTS

WO WO 99/42919 8/1999

* cited by examiner

*Primary Examiner* — Dismery Mercedes
(74) *Attorney, Agent, or Firm* — Schiff Hardin LLP

(57) ABSTRACT

An input device to control elements of graphical user interfaces has at least one input element with multiple buttons (keys), and at least one rotatable input element that is actuated at least along one essentially horizontal axis, and at least one elevation (18) that extends essentially perpendicular to a primary extension plane of the input device. The elevation is provided with at least one additional input element and the additional input element is rotatable around an essentially vertical axis.

6 Claims, 2 Drawing Sheets

INPUT DEVICE TO CONTROL ELEMENTS OF GRAPHICAL USER INTERFACES

BACKGROUND OF THE INVENTION

1. Field of the Invention

The invention concerns an input device to control elements of a graphical user interface, the input device being of the type having at least one input element with a number of actuatable buttons, and at least one rotatable input element that is actuated at least along one substantially horizontal axis.

2. Description of the Prior Art

Large quantities of data (radiological data sets or data objects) are regularly acquired in the implementation of imaging methods in medical technology (for example magnetic resonance tomography, computed tomography etc.). Various methods (known as browsers) are known for the necessary inspection, processing and assessment of these acquired data. These browsers for radiological data sets allow the presentation of the data sets in various views for the user (radiologist, MRTA).

These browsers are normally operated via a graphical user interface (GUI). The high functionality of current browser applications is often reflected in sophisticated and elaborate GUIs. However, these GUIs generally display only a small portion of the available functions. Most of the additional available functions can only be displayed via indirect paths, for example by context menus or additional graphical elements (known as panels) that can be overlaid and hidden.

The current typical input device for GUIs is primarily a mouse (or related devices such as trackballs or touchpads) that is operated with one (normally the dominant) hand. In specific situations, a keyboard is added. This primarily occurs for text input, but keyboard shortcuts (hotkeys) are often also used. These keyboard shortcuts are used for the most part to directly activate functions that are difficult to access or frequently necessary. However, for the vast majority of the operating processes the input is based exclusively on the (one-handed) use of the mouse or comparable input devices.

This mode of operation is often not only subjectively perceived by users to be suboptimal, but additionally contradicts objective scientific models according to which the person preferably and more efficiently uses both hands in a parallel or serial asymmetrical work process (dominant hand: manipulation; non-dominant hand: context/administration of tools).

Since the operation of GUIs by means of an asymmetrical, one-handed input has its weaknesses (low efficiency, among other things, but also lopsided physical stress of the body, low comfort), input devices for the non-dominant hand have been developed for specific application fields (3D navigation). However, these input devices exhibit the disadvantage that they cannot be applied for use in the aforementioned browsers.

Devices of the cited type are described in DE 600 31 928 T2, which pertains to an input device and information processing device. The input device has a handle part and a pointer part. The handle part possesses a rotation part that can be depressed by an arbitrary finger of the user.

A multi-dimensional input device is known from DE 11 2006 001 161 T5, which has a first, second and third sensors that respectively correspond to different degrees of freedom, and generate multiple signals.

A pointer control with a control stud (peg) and a hand rest is known from WO 99/42919. The device is equipped with a hand rest that brings the hand and the fingers into a position that is suitable for the operation of the control stud.

SUMMARY OF THE INVENTION

An object of the invention is to provide an ergonomically optimized input device to control elements of graphical user interfaces, with which input device the usage comfort is increased and with which the manipulation of additional degrees of freedom is intuitively enabled.

The invention is based on the fact that the input device has multiple different input elements to control elements of graphical user interfaces, which input elements are associated with specific functions so that the operation/control of a browser can ensue in a parallel or serial asymmetrical work process. Among these input elements is an input element that can be rotated on a vertical axis so that it can be precisely and finely adjusted—in particular with thumb and index finger—for manipulation of parameters.

The input device according to the invention for the control of elements of graphical user interfaces has at least one input element having multiple buttons (keys), at least one rotatable input element, wherein the rotatable input element is actuated at least along one essentially horizontal axis, and/or at least one elevation that extends essentially perpendicular to a primary extension plane of the input device, the elevation being provided with at least one additional input element, and/or the additional input element is actuated at least along one essentially vertical axis.

One or more of the following features are advantageously provided in the embodiments of the method:

- the input device also has multiple sensors, wherein an inclination change of the input device relative to a reference plane is detected via the output signals,
- the rotatable input elements detect at least one essentially rotatory and/or at least one essentially translational movement,
- the additional input elements detect at least one essentially rotatory and/or at least one essentially translational movement,
- the multiple buttons of the input device can be freely configured,
- the detection of the inclination change ensues by means of pressure sensors,
- multiple buttons of the input device form a numerical keypad.

An advantage of the invention is that the display elements (symbols, icons, panels, windows etc.) used on a graphical user interface can be directly manipulated by means of the input device according to the invention, i.e. without the input from keyboard shortcuts or hotkeys.

The input device according to the invention also supports a two-handed, asymmetrical mode of operation within graphical user interfaces and simultaneously allows the direct control of specific elements (for example tools, lists, panels, input fields etc.) under consideration of the current context.

Additional advantages of the input device according to the invention are also:

more efficient operation:

According to the evidence, the two-handed, asymmetrical operation is faster than a comparable one-handed interaction.

lower cognitive stress:

By sparing interactions and via the better utilization of a simplified user interface (via simpler hiding and overlaying of elements), the cognitive stress of the user is significantly reduced.

lower physical stress:

Corresponding overstraining by the user is prevented via the distribution of the workload to two arms/hands.

greater user comfort:

The simultaneous use of two hands also corresponds to real work situations. The user can better make use of his physical [body] perception and finds the work process to be significantly more comfortable.

An additional aspect of the invention concerns a computer program with which it is possible to configure the buttons and/or input elements of the input device when said computer program runs on a computer.

DESCRIPTION OF THE PREFERRED EMBODIMENTS

The input device according to the invention utilizes the possibilities to arrange multiple input elements ergonomically so that that the input elements can be operated in an efficient manner.

Figure 1:
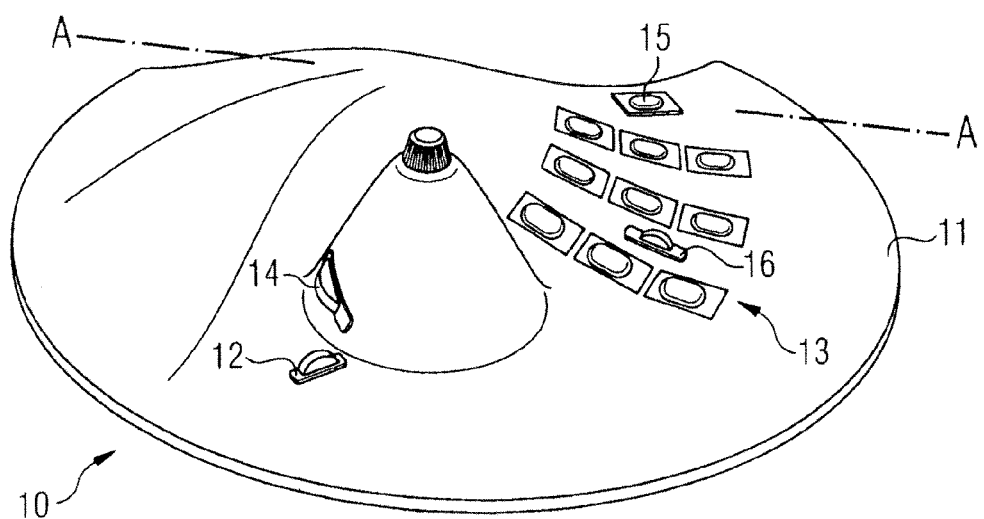
FIG. 1 is a perspective view of the input device according to the invention.

FIG. 1 shows an embodiment of the input device 10 according to the invention. The input device 10 has an essentially flat surface 11 that possesses an essentially circular circumference. The input device 10 also has multiple input elements 12-17. The input elements 13a-13i form a 3×3 keypad similar to a numerical keypad. The input elements 12, 14 and 16 are fashioned as elements known as scroll wheels. The scrolling in graphical user interfaces and/or the focus in lists can be moved by means of scroll wheels without moving the input device 10. The scroll wheels can also have additional degrees of freedom in the horizontal and/or vertical direction. The input device 10 also exhibits an elevation 18 or projection that is essentially fashioned in the shape of a cone. An additional input device 17 is arranged on the elevation 18. The input device 17 is arranged such that it can rotate around an essentially vertical axis.

Figure 2:
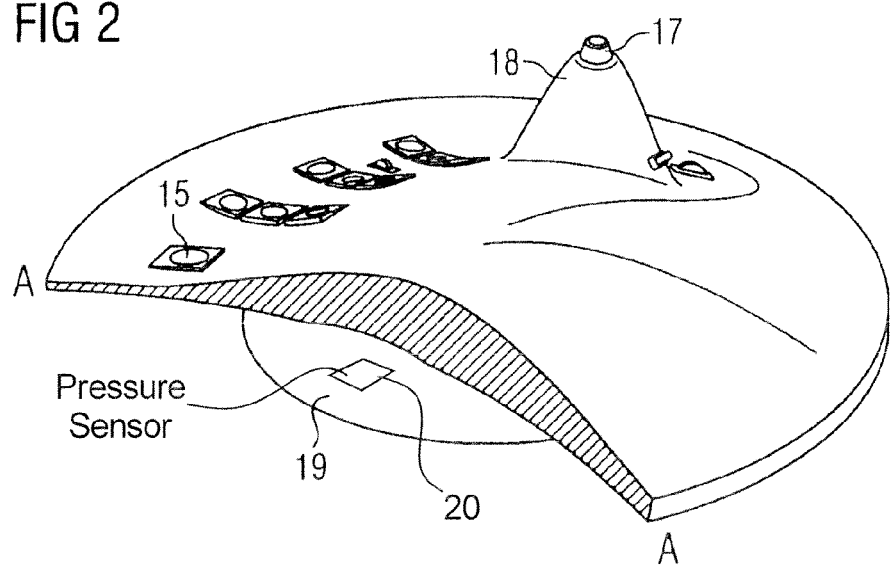
FIG. 2 is a section view of the input device according to the invention.

The input device 10 according to the invention is shown from a different perspective in FIG. 2, with a section along the line A-A in FIG. 1. Via the section along the line A-A it is recognizable that the essentially flat surface 11 exhibits a variation in its diameter. The stability of the surface 11 is increased by this embodiment, which also enables an ergonomic embodiment of the surface 11. Multiple pressure sensors (not shown) are arranged in an input element 19 on the side of the surface 11 opposite the input device 13. The input element 19 is formed of an elastic material. By exerting pressure on the input device 10 in different directions (right, left, forward, back), the input device 10 can be tilted slightly on an axis situated essentially perpendicular to a reference plane. The reference plane can be any substrate on which the input device is located. Pressure sensors (not shown) are triggered by specific weight displacement of the hand and the tilting of the input device 10 that result from this. For example, among other things elements on graphical interfaces—for example panels on the left or, respectively, right screen edge, or frequently used dialog boxes, applets—can be overlaid and hidden by means of the signals output by the pressure sensors.

Figure 3:
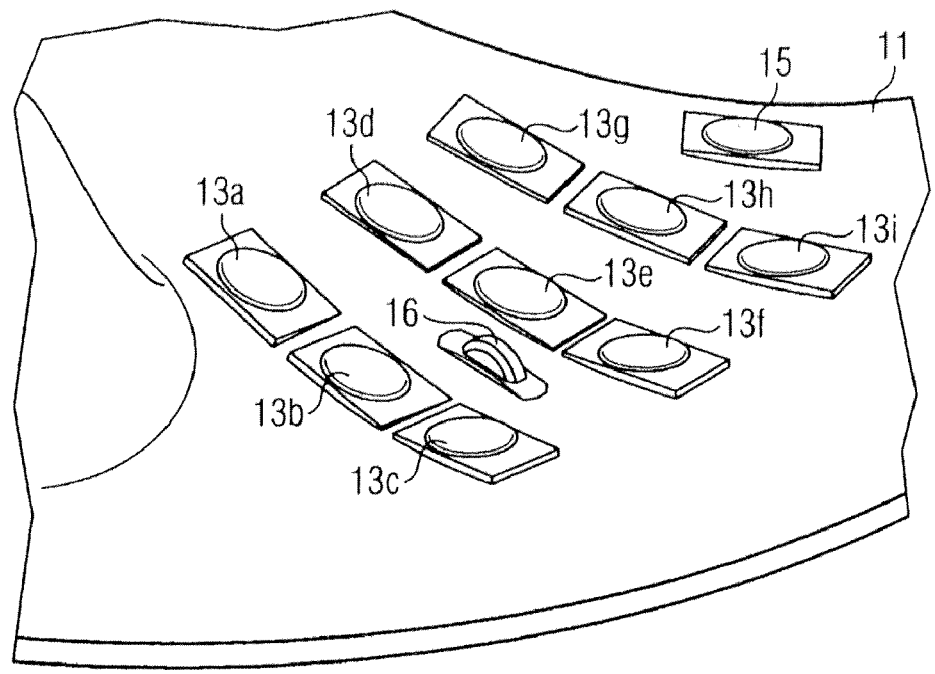
FIG. 3 is a detail of multiple input elements.

FIG. 3 shows a detail view of the keypad 13. The keypad 13 has 9 buttons 13a-13i. The buttons enable the input of numbers (1-9) or program-specific or user-specific hotkeys or macros depending on the current usage context. A macro is thereby a sequence of commands stored in advance. A hotkey is an arbitrary key combination (also a keyboard shortcut, key sequence, keyboard combination, keyboard command) stored in advance. A scroll wheel 16 is located in the region of the keypad. This scroll wheel 16 can alternately be reached and operated by the index or middle finger. The tools used most frequently can thus be directly selected with the scroll wheel 16.

Figure 4:
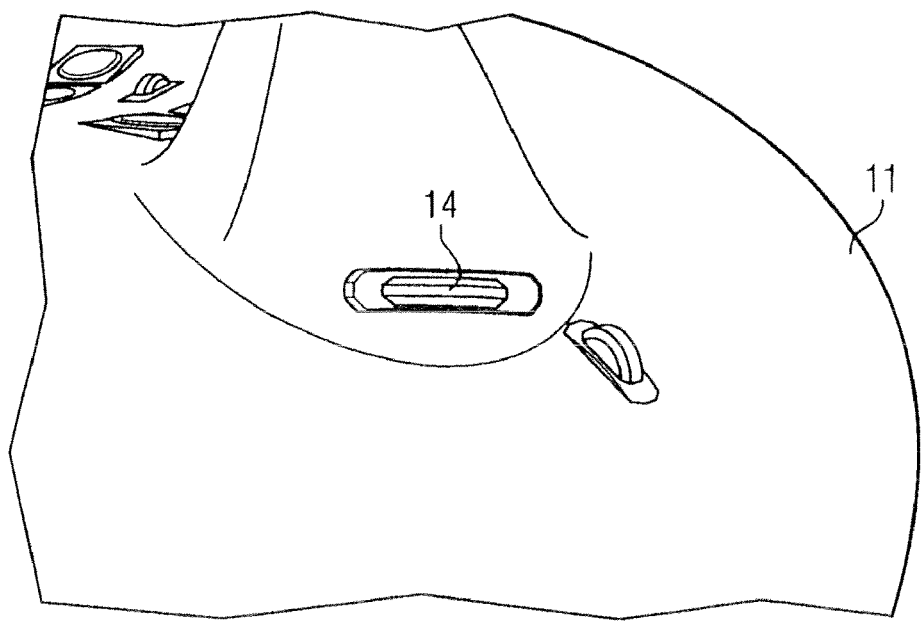
FIG. 4 is a further detail of multiple input elements.

An additional detail view of the input device 10 according to the invention is shown in FIG. 4. It is recognizable from FIG. 4 that the scroll wheels 12 and 14 are arranged essentially at right angles to one another. With this arrangement it is possible to control the horizontal scrolling with the one scroll wheel and the vertical scrolling with the other scroll wheel. It is also possible to associate other commands/controls with the scroll wheels 14, 16.

An input device was described to control elements of graphical user interfaces, with: at least one input element possessing multiple buttons; at least one rotatable input element, wherein the rotatable input element is actuated at least along one essentially horizontal axis; at least one elevation that extends essentially perpendicular to a primary extension plane of the input device, wherein the elevation is provided with at least one additional input element and the additional input element is actuated at least along one essentially vertical axis.

The aforementioned embodiments can be implemented as software modules and/or hardware modules in the corresponding function blocks. It is also noted that the present invention is not limited to the aforementioned embodiments, rather can also be applied in other methods and devices to implement a medical examination via a user interface.

Although modifications and changes may be suggested by those skilled in the art, it is the intention of the inventors to embody within the patent warranted hereon all changes and modifications as reasonably and properly come within the scope of their contribution to the art.

We claim as our invention:

1. An input device to control elements of a graphical user interface, said input device comprising:

a manually manipulable base element carrying a plurality of actuatable buttons that, when manually actuated, emit first control signals, respectively, to said graphical user interface;

at least one rotatable input element carried by said base element, said rotatable input element being manually actuatable at least along a substantially horizontal axis to emit a second control signal to said graphical user;

said base element having a base element surface comprising a conical surface elevation that extends substantially perpendicular to a primary plane of said base element, said conical surface elevation carrying at least one additional input element at a location on said conical surface elevation that is elevated highest from said primary plane by said conical surface elevation;

said additional input element being rotatable around a substantially vertical axis proceeding through said surface elevation, to emit a third control signal to said graphical user interface dependent on the rotation of said additional element;

a resilient mount on which said base element is mounted beneath said base element surface, allowing tilting of said base element together with said base element surface thereof, on said mount relative to a reference plane; and a plurality of pressure sensors in said mount that respectively emit pressure sensor output signals to said graphical user interface in response to said tilting of said base element on said mount, that respectively identify an inclination change, in respectively different directions, of said base element resulting from said tilting relative to said reference plane, said pressure output signals being fourth control signals that are respectively dependent on said inclination change in a respective direction.

2. An input device as claimed in claim 1 wherein said sensors are pressure sensors.

3. An input device as claimed in claim 1 wherein said at least one rotatable input element detects a movement selected from the group consisting of a rotary movement and a translational movement.

4. An input device as claimed in claim 1 wherein said additional input element detects movement selected from the group consisting of rotary and translational movement.

5. An input device as claimed in claim 1 wherein said multiple actuatable buttons are freely configured on said base element.

6. An input device as claimed in claim 1 wherein said plurality of actuatable buttons form a numerical keypad.

* * * * *